(12) United States Patent
Nakatani (10) Patent No.: US 7,018,545 B2
(45) Date of Patent: Mar. 28, 2006

(54) COMPONENT SEPARATING DEVICE, METHOD OF MANUFACTURING THE DEVICE, AND METHOD OF SEPARATING FINE SOLID COMPONENT BY USING THE DEVICE

(75) Inventor: Masaya Nakatani, Hyogo (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 138 days.

(21) Appl. No.: 10/491,753

(22) PCT Filed: Jul. 9, 2003

(86) PCT No.: PCT/JP03/08714

§ 371 (c)(1),
(2), (4) Date: Apr. 5, 2004

(87) PCT Pub. No.: WO2004/009240

PCT Pub. Date: Jan. 29, 2004

(65) Prior Publication Data

US 2005/0000912 A1    Jan. 6, 2005

(30) Foreign Application Priority Data

Jul. 22, 2002    (JP)    ................ 2002-212031

(51) Int. Cl.
*B01D 35/06*    (2006.01)

(52) U.S. Cl. .................. 210/748; 204/554; 204/571; 204/660

(58) Field of Classification Search ............. 210/748; 204/554, 571, 660
See application file for complete search history.

(56) References Cited

U.S. PATENT DOCUMENTS

| 4,710,161 A | 12/1987 | Takabayashi et al. |
| 6,537,437 B1 * | 3/2003 | Galambos et al. ......... 204/600 |
| 2002/0021055 A1 | 2/2002 | Lee et al. |

FOREIGN PATENT DOCUMENTS

JP    11-346482    12/1999

OTHER PUBLICATIONS

Y. Yoon et al., "Integrated Vertical Screen Microfilter System Using Inclined SU-8 Structures", 2003 IEEE, pp. 227-230.

* cited by examiner

*Primary Examiner*—Robert A. Hopkins
(74) *Attorney, Agent, or Firm*—Wenderoth, Lind & Ponack, L.L.P.

(57) ABSTRACT

A components separation device including well (2) for containing a sample, being an object of separation, which well (2) is disposed on stage (1). Well (2) is fixed at only one point of the bottom on stage (1). Base (13) formed on stage (1) is further provided with an actuator for vibrating well (2).

15 Claims, 10 Drawing Sheets

COMPONENT SEPARATING DEVICE, METHOD OF MANUFACTURING THE DEVICE, AND METHOD OF SEPARATING FINE SOLID COMPONENT BY USING THE DEVICE

TECHNICAL FIELD

The present invention relates to a device for separating a solution consisting of liquid substances and solid substances, typical examples of such a solution being the blood, the milky liquid, etc., into the constituent components, and for separating a mixture of a plurality of solid substances, or grains, into respective solid micro components having different mass or size. A method for manufacturing such separation device, and a method of separation using the device are also disclosed in the invention. It can be used in a solid micro components separator, an ingredients analyzer and the like kinds of apparatus.

BACKGROUND ART

The river waters, the sea waters, the blood, etc. are the examples of a fluid, or a powdery fluid, consisting of a mixture of a plurality of solid components. These are the mixture of liquid components and solid components; although the solid components such as sand grains, germs, blood cells may precipitate or disperse in liquid component, they do not dissolve into the liquid component, but they keep on staying as the solid components.

The conventional method of separating it into a plurality of constituent components is described in the following, taking a blood cell/blood plasma separator as the example.

A blood sample is normally made available in the form of a whole blood which is consisting of blood plasma, or the liquid component, blood cells, or the solid component, and others. In most of the practical occasions for use as the test specimen, however, only the portion of blood cells, or the blood plasma, is needed.

In examining the blood sugar value of a blood, for example, the content of blood sugar dissolved in blood plasma is the subject of inspection; while for the detection of a DNA, it needs to be taken out of a white blood cell in the blood. It has been a conventional practice to put a sample of the whole blood in a test tube, and apply a centrifugal force. Each of constituent components of the whole blood in the test tube undergoes different centrifugal force, and the components are separated in accordance with the mass.

The blood plasma can be taken out when the supernatant liquid is extracted, while the blood cells can be taken out from the precipitate. The respective portions thus separated are used as the sample of examination for the specific purpose.

There is another method using a filter, for separating a sample of very small amount.

This is the method disclosed by Yong-Kyu Yoon, et. al. The method makes use of the porosity of a filter; where, blood plasma is made available by filtering blood cells larger than a certain specific size, or blood cells are taken out otherwise. The separation characteristic of the method depends on the size and the number of holes, etc. of a filter. Therefore, the design of a filter needs to be optimized for a targeted component of separation. A typical method for providing a mesh filter with a good reproducibility in terms of the size and numbers is exposing a photo-sensitive resist in a three dimensional arrangement.

However, the described previous method by means of centrifugal separation has the following problems. Namely, a sample of whole blood has be put into such a vessel as a test tube for the separation by centrifugal force; which means that a test tube needs to be filled with a certain amount of whole blood, viz. a sample of whole blood is needed for several to several tens of milliliters. Thus it is difficult to use the method for the samples of very small amount.

Meanwhile, the filtering method, which traps, or allows, solid grains of a certain size to go through when a fluid, or a powdery fluid, consisting of a mixture of a plurality of components is forced to pass through a filter, has a problem that the existence of solid particles of different sizes makes separation of components difficult. Namely, when a filter which has been designed to allow only small particles to go through is used in order to take out the particles of a certain specific size, the particles larger than the size of the small particles are trapped by the filter to cause a clogged filter. As the result, passing of the small particles is blocked.

DISCLOSURE OF INVENTION

A solid micro components separation device in the present invention includes a stage, a well having a certain specific volume disposed on the stage, and a base fixed on the stage. The base and the well are connected by an actuator. A sample consisting of at least two different kinds of solid micro components can be put in the well. The separation device can separate the sample into solid micro components even if the volume of the sample is very small.

A method for manufacturing the components separation device in accordance with the present invention includes the steps of forming by an etching process a cavity and a base on a glass stage; bonding a silicon substrate on the glass stage by direct bonding; providing by sputtering or vacuum deposition a lower electrode, a piezoelectric layer and an upper electrode, in the order, on the bonded silicon substrate to form an actuator; patterning the upper electrode, piezoelectric layer and lower electrode by etching; and forming by etching the silicon substrate a well and a supporting member on the upper part of the cavity.

A method of separating a sample into solid micro components uses a components separation device in the present invention. A sample consisting of solid components and liquid components is placed in the well, and then the actuator vibrates the well so that different constituent components contained in the sample are distributed unevenly in the well. In the present separation method, a sample of very small amount can be separated precisely into respective solid micro components.

DETAILED DESCRIPTION OF PREFERRED EMBODIMENTS

A solid micro components separation device in the present invention holds a sample, which is consisting of a plurality of components, within a silicon well. An actuator provides the sample with vibration, and the constituent components of the sample are separated against each other as the result of difference in their response to the vibration. The well can be implemented in the form of a very small vessel, because it is provided by processing a silicon substrate. Means to vibrate the well is also provided by processing the silicon substrate. Therefore, the total device can be a very compact one. For separating various kinds of mixed components, the vibrating conditions to be given to the well may be changed; so that the mode of vibration corresponds to a certain targeted component. Therefore, a separation device in the present invention can be a versatile separator for separating solid micro components, as compared to a filter type separator which is dedicated to separating a certain specific component.

Practical examples of components separation device are described in accordance with exemplary embodiments of the present invention, with reference to the drawings.

FIRST EXEMPLARY EMBODIMENT

Figure 1:
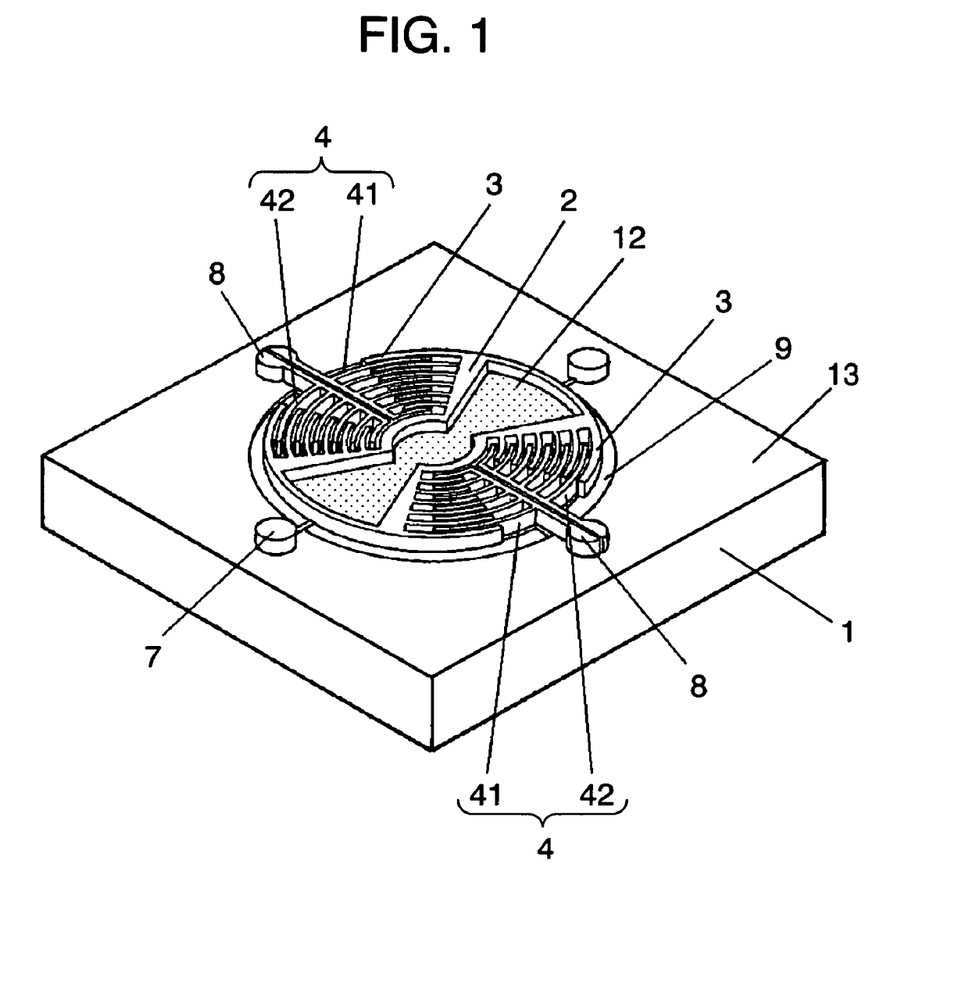
FIG. 1 shows a perspective view of a components separation device in accordance with an exemplary embodiment of the present invention.
Figure 2:
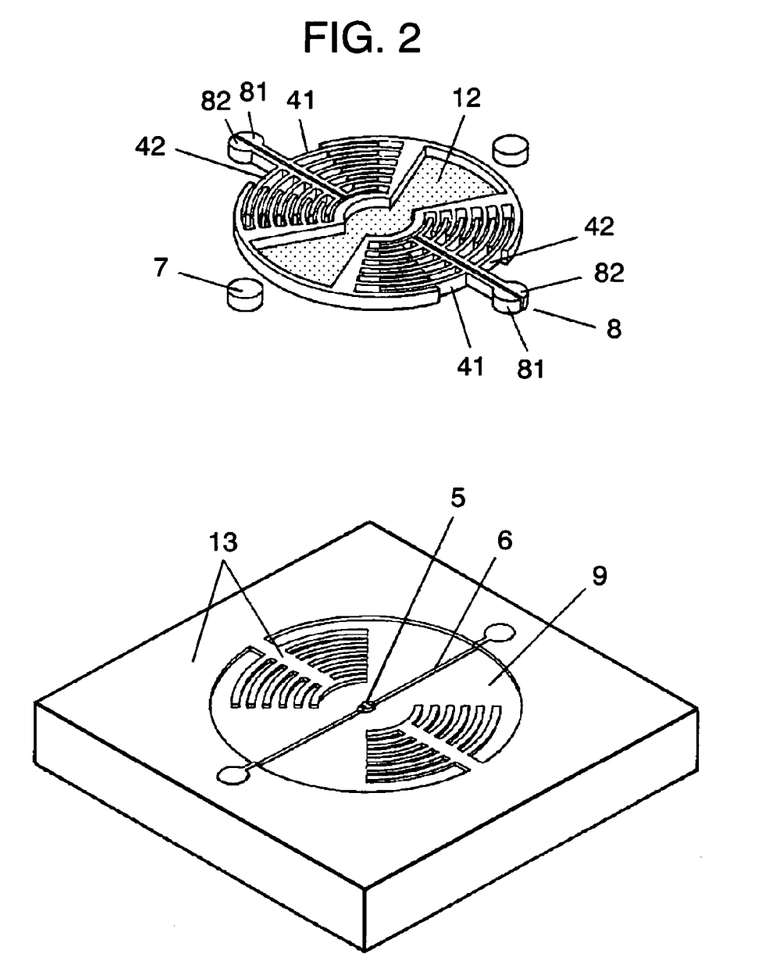
FIG. 2 shows an exploded perspective view of a components separation device in accordance with an exemplary embodiment of the present invention.

FIG. 1 and FIG. 2 show the configuration of a solid micro components separation device in the present invention. Provided on glass stage 1 are glass cavity 9, glass base 13 and central axis 5. As shown in FIG. 2, glass base 13 is consisting of a comb-teeth portion and a stepped portion. Well 2 formed of silicon is connected via central axis 5 on glass cavity 9. So, well 2 can vibrate in the rotating direction around central axis 5. Namely, the well bonded on the central axis can vibrate in the direction of twisting around the central axis. A part of well 2 forms movable comb-teeth electrode 3.

Movable comb-teeth electrode 3 opposes to fixed comb-teeth electrodes 41, 42, which are made of silicon, and functions as an actuator to pull well 2 which contains movable comb-teeth electrode 3. Well 2 is connected with common electrode 6 provided on central axis 5, and movable comb-teeth electrode 3 is connected via common electrode 6 with common electrode pad 7 provided on stage 1. The silicon material used here is provided with an electrical conductivity of a certain level for functioning as an electrode.

Fixed comb-teeth electrode unit 4 on glass base 13 is divided at the center into fixed comb-teeth electrodes 41 and 42 arranged symmetrical to each other, as illustrated in FIG. 1 and FIG. 2. Fixed comb-teeth electrodes 41 and 42 are led, respectively, to individual electrode pads 81 and 82 provided on stage 1. When fixed comb-teeth electrodes 41 and 42 are applied with a certain voltage via individual electrode pads 81 and 82, the actuator formed by the opposing electrodes generates an electrostatic force, and well 2 moves around central axis 5. When the voltage applied on individual electrode pads 81, 82 is changed cyclically, well 2 makes a rotating vibration around central axis 5.

(How to use 1)

Figure 3:
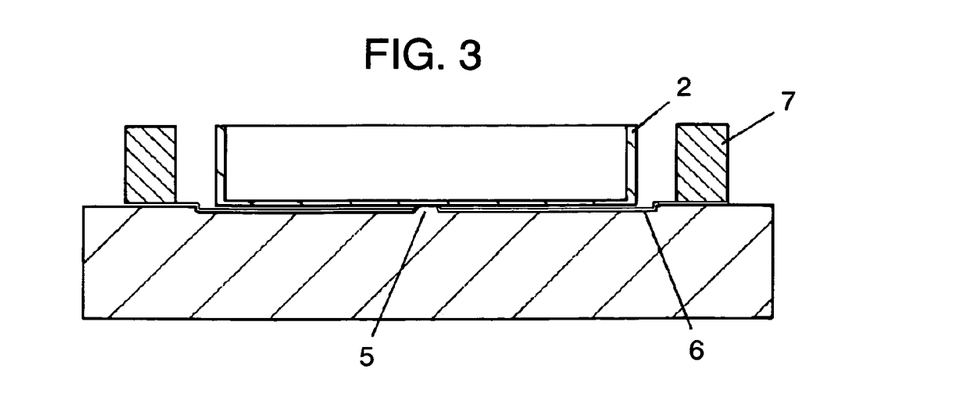
FIG. 3 is a cross sectional view, used to describe the operation of a components separation device in accordance with an exemplary embodiment of the present invention.
Figure 4:
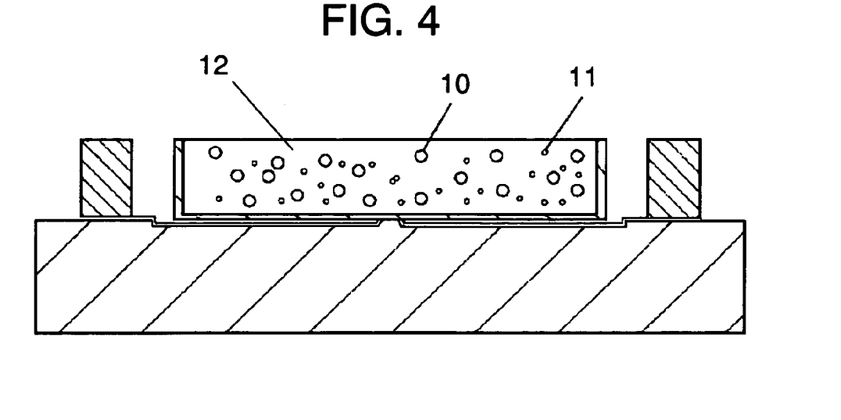
FIG. 4 is a cross sectional view of a components separation device in accordance with an exemplary embodiment of the present invention.
Figure 5:
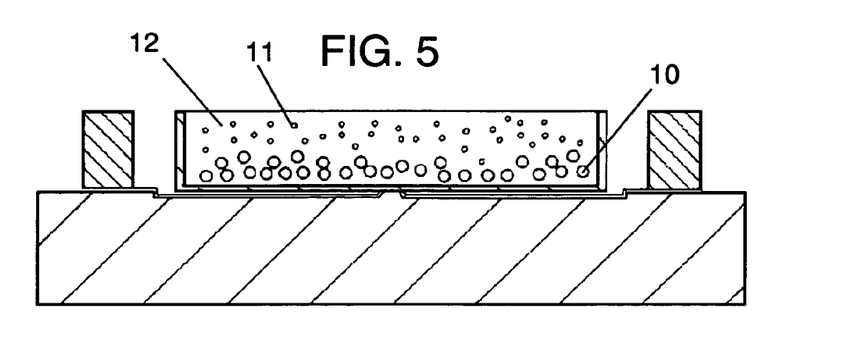
FIG. 5 is a cross sectional view of a components separation device in accordance with an exemplary embodiment of the present invention.

A procedure how to separate liquid, or solid, components among a mixture containing different components is described using a solid micro components separation device in accordance with the present embodiment. FIG. 3 through FIG. 5 show cross sectional models of a solid micro components separation device, used to describe the process of separation.

As shown in FIG. 4, a mixture of solid particles which contains solid components 10 and solid components 11 is put in the inside of silicon cavity 12 of well 2 illustrated in FIG. 3. At the initial stage, these components are in the mixed state as shown in FIG. 4. When electrode pads 81, 82 (not shown in FIG. 4) are applied with a cyclically changing voltage, well 2 starts making a rotating vibration around central axis 5. Acceleration due to the rotating vibration causes inertial force with solid components 10 and 11 stored in well 2. The inertial forces caused with respective components differ depending on the mass of components. Difference also exists in the force of mutual friction between respective components. The differences in these forces lead the components to an uneven distribution within silicon cavity 12; for example, solid components 10 and solid components 11 are separated to the upward and to the downward respectively, as illustrated in FIG. 5.

Although the descriptions in embodiment 1 have been based on a sample in which different solid components are mixed, the present method of separating solid micro components works likewise for separating other groups of samples which contain, for example, solid components and liquid components, or liquid components and liquid components, in so far as each of the components does not resolve among each other.

(How to manufacture 1)

A process to manufacture a solid micro components separation device is described referring to FIG. 6 through FIG. 11.

Figure 6:
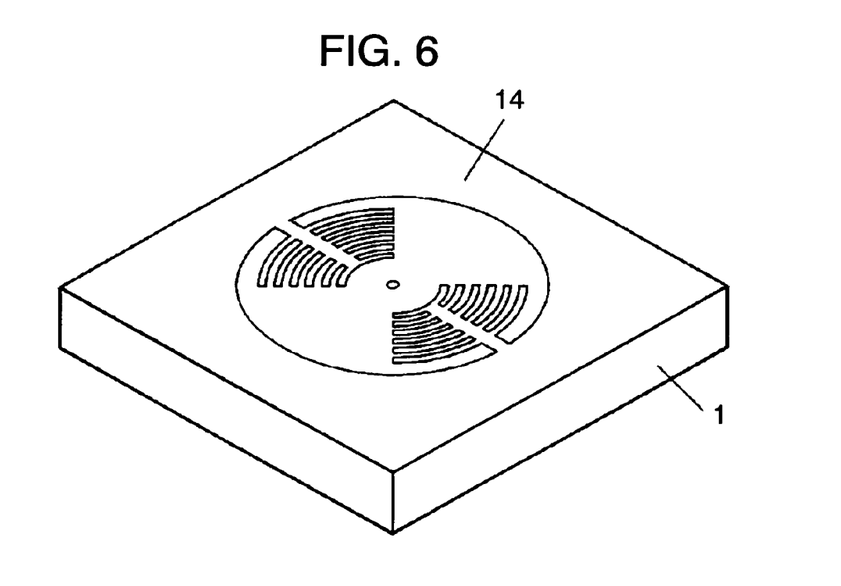
FIG. 6 is a perspective view of a components separation device, used to describe a method for manufacturing it in accordance with an exemplary embodiment of the present invention.
Figure 7:
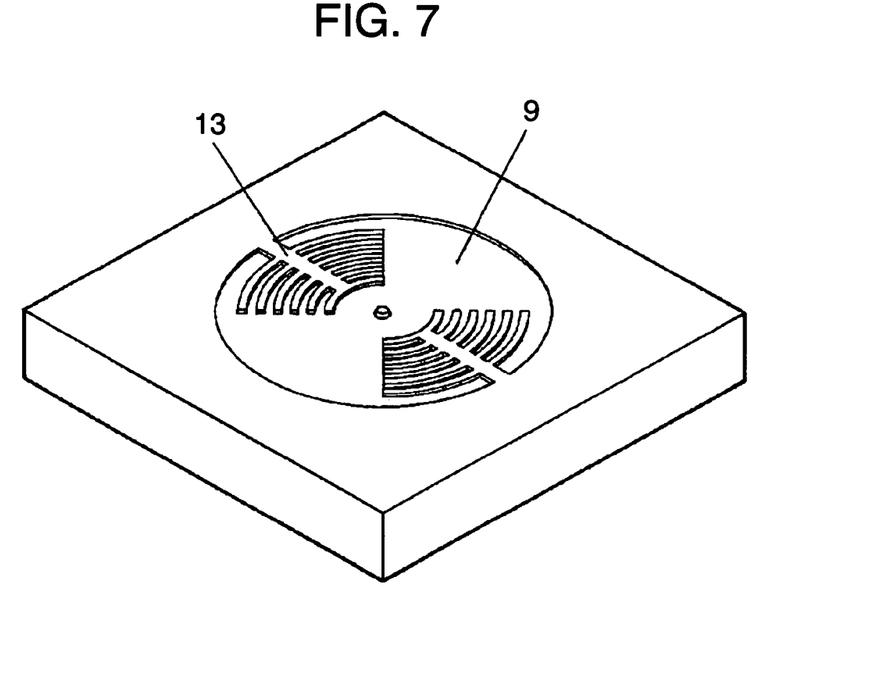
FIG. 7 is a perspective view of a components separation device, used to describe a method for manufacturing it in accordance with an exemplary embodiment of the present invention.

As shown in FIG. 6, stage 1 of a glass substrate is provided with resist mask 14 of a certain specific pattern. Glass cavity 9 is etched, as shown in FIG. 7, at the same time, glass base 13 and central axis 5 are also formed. The pattern of glass base 13 is consisting of a portion having the same shape as fixed comb-teeth electrode unit 4 and a surrounding stepped portion. Either the dry etching or the wet etching process may be used for the etching.

Figure 8:
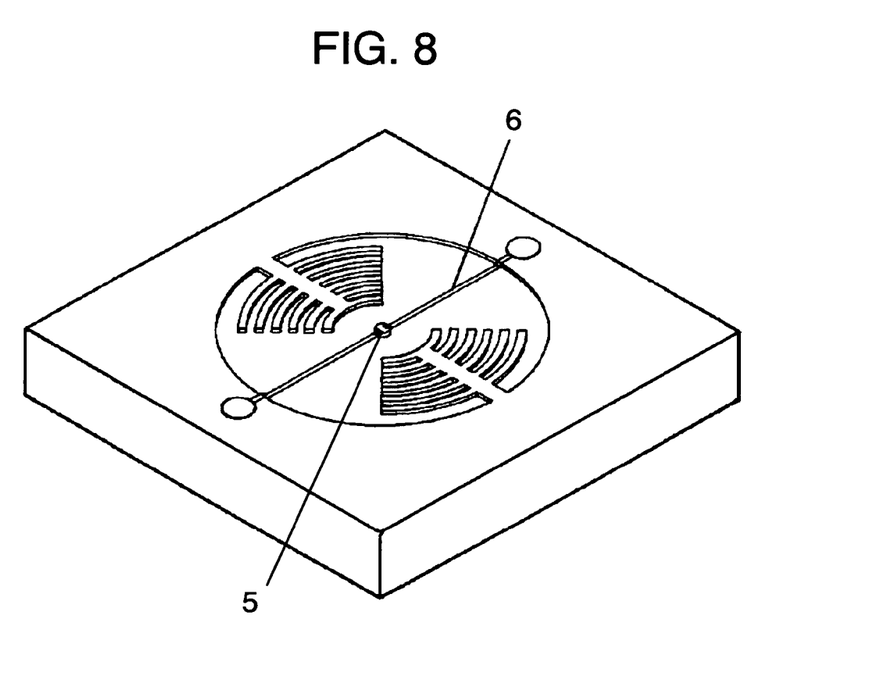
FIG. 8 is a perspective view of a components separation device, used to describe a method for manufacturing it in accordance with an exemplary embodiment of the present invention.

Then, as shown in FIG. 8, common electrode 6 is formed using gold. The electrode is formed in a pattern so that it covers at least a part of central axis 5. In the present embodiment, it has been formed to cover a part of the edge of the central axis. The reason why it is formed in the above-described pattern will be detailed later; describing simply, it is for bonding a silicon substrate by the direct bonding without using any adhesive agent. The gold electrode may be formed through a generally known process, such as sputtering, vacuum deposition, etc. The alternative materials, besides gold, for common electrode 6 include chromium, titanium, platinum, etc.

Figure 9:
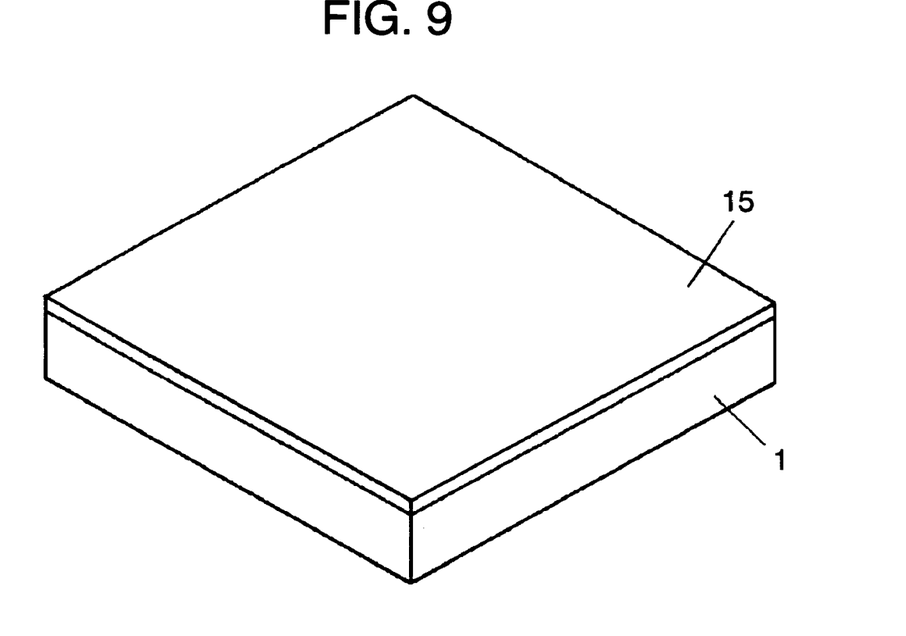
FIG. 9 is a perspective view of a components separation device, used to describe a method for manufacturing it in accordance with an exemplary embodiment of the present invention.

Then, as shown in FIG. 9, silicon substrate 15 is bonded on stage 1, by means of the direct bonding.

The surfaces of stage 1 and silicon substrate 15 are thoroughly cleaned before they are bonded together, using e.g. an acidic liquid of mixed sulfuric acid and hydrogen peroxide solution, or other alkaline liquid, so that there is no stain or dust remaining on the surfaces. Normally, the cleaning with the above-described acidic liquid is sufficient; however, there are some exceptional cases where the bonding is not possible depending on the surface roughness with the silicon and the glass. In such a case, the use of an alkaline liquid sometimes proves to be effective. An alkaline liquid etches silicon and glass, if slightly; so, a long time cleaning is not preferred. According to experimental results, it has been confirmed that a short time cleaning of approximately 10 min. results in a favorable bonding.

After the above cleaning is finished, stage 1 and silicon substrate 15 are put together and then heated at 200–500° C. Then, the interatomic bonding takes place between the silicon and the glass. The stage and the silicon substrate are bonded fast by the interatomic bonding. Silicon substrate 15 is bonded only at the regions of glass base 13 and the surface of central axis 5 on glass stage 1. The portion of central axis 5 where common electrode 6 is formed with gold or chromium is not bonded with silicon substrate 15. However, the bonding is not ill-affected if the area of common electrode 6 is sufficiently small in relation to the glass-exposed area of central axis 5. Since common electrode 6 provided on central axis 5 makes a pressure contact with silicon substrate 15 at a sufficiently high pressure, silicon substrate 15 and common electrode 6 are electrically connected. The use of gold for common electrode 6 provides the most favorable electrical connection. Namely, when gold and silicon in a tight contact state are heated to 400–500° C., the gold atoms diffuse into silicon. This further enhances the bonding strength between central axis 5 and silicon substrate 15, and ensures the electrical connection.

Figure 10:
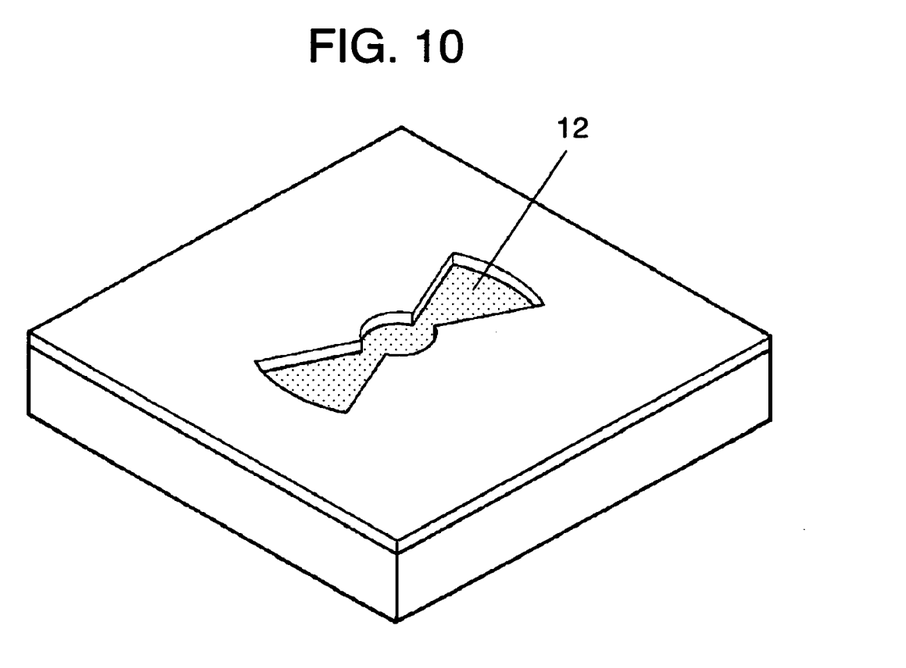
FIG. 10 is a perspective view of a components separation device, used to describe a method for manufacturing it in accordance with an exemplary embodiment of the present invention.

Next, as shown in FIG. 10, silicon cavity 12 is formed by dry-etching silicon substrate 15 to a certain specific pattern from the above. At this stage, it is essential to control the etching depth to a certain specific value, so as not to etch silicon substrate 15 through.

Figure 11:
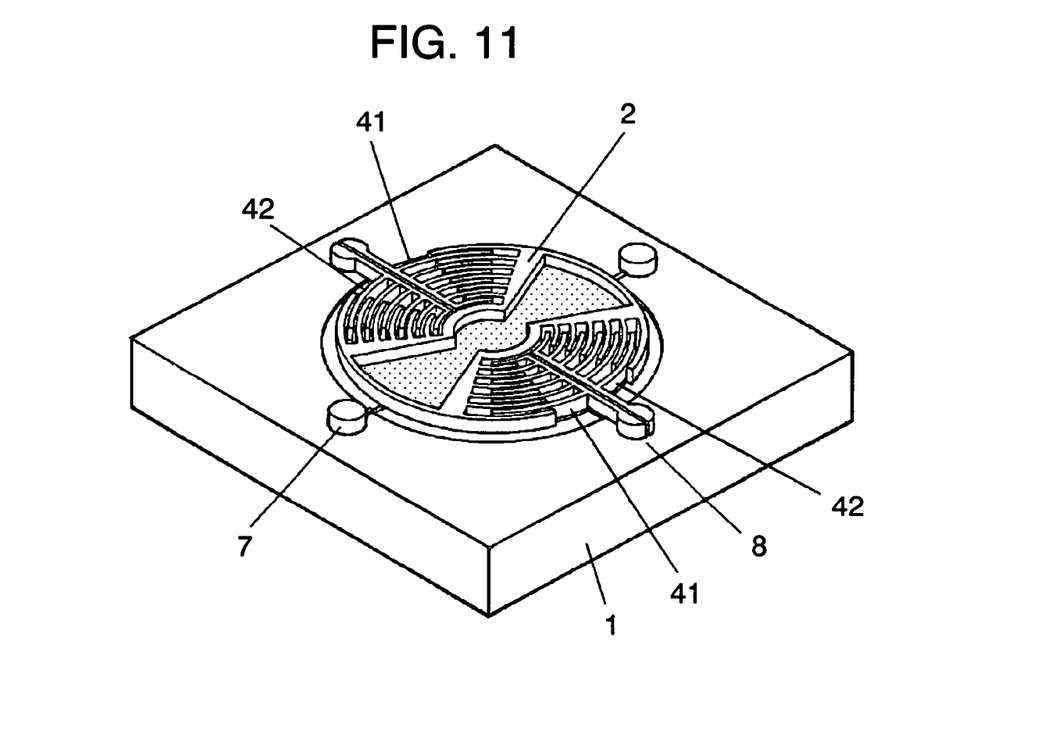
FIG. 11 is a perspective view used to show the process of manufacturing a components separation device in the present invention.

Finally, as shown in FIG. 11, silicon substrate 15 is dry-etched to a certain specific pattern for forming well 2, fixed comb-teeth electrode unit 4, movable comb-teeth electrode 3, common electrode pad 7 and electrode pad 8. Silicon substrate 15 is etched through for these patterns.

When a solid micro components separation device thus finished is applied with a certain voltage at individual electrode pads 81 and 82, which have been electrically connected with respective fixed drive electrodes 41 and 42, an electrostatic pulling force is generated between movable comb-teeth electrode 3 and fixed comb-teeth electrodes 41, 42. Well 2 is vibrated in a rotating direction around central axis 5 due to the electrostatic force.

As described in the above, a solid micro components separation device in accordance with embodiment 1 of the present invention includes well 2 made of silicon for receiving a sample in the liquid or solid state provided on stage 1, which is made of glass. Well 2 is fixed to stage 1 at only one point at the bottom. An actuator is structured between glass base 13, which is made of glass, provided on stage 1 and well 2, in order to vibrate well 2. Sample liquid in silicon cavity 12 is vibrated by the actuator, and separated into respective components because of the difference in their response to the vibration.

Well 2 is provided by etching silicon substrate 15, so it can be formed in the shape of a very small vessel; and the means to vibrate it is also formed simultaneously out of silicon substrate 15. Thus the separation device can be fabricated into a compact device.

Stage 1 and glass base 13 are formed with glass material, while well 2 is formed with silicon substrate 15. Since there is a significant difference in the etching rate between the two materials, the shapes can be controlled at a high precision level. Thus a compact high-precision device can be implemented.

For separating various kinds of components, the state of vibration given to well 2 may be changed to correspond to a certain targeted component. Therefore, a solid micro components separation device in the present embodiment is a versatile separator for separating solid micro components, as compared to the filter type separator which is dedicated to a certain specific target.

A solid micro components separation device described in embodiment 1 can be applied to such a separator where cell components can be separated in radial direction, or concentric direction.

SECOND EXEMPLARY EMBODIMENT

A solid micro components separation device in accordance with a second exemplary embodiment is described below, referring to FIG. 12 and FIG. 13.

Figure 14:
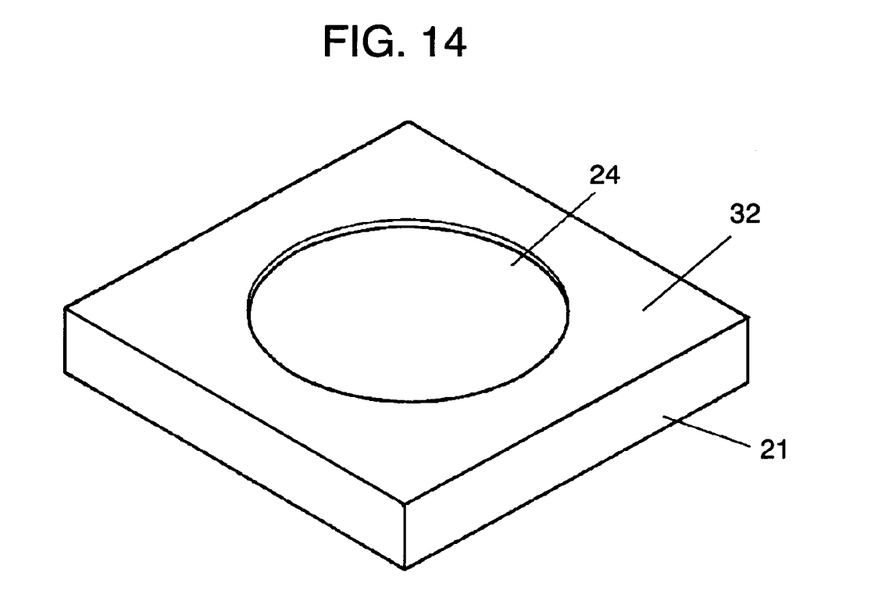
FIG. 14 is a perspective view of a components separation device, used to describe a method for manufacturing it in accordance with an exemplary embodiment of the present invention.

As shown in FIG. 14, glass cavity 24 and glass base 32 are provided on glass stage 21. Silicon well 23 and silicon cavity 25 are provided in the inside of glass cavity 24.

The point of difference from embodiment 1 is in the structure of an actuator for vibrating well 23.

Figure 12:
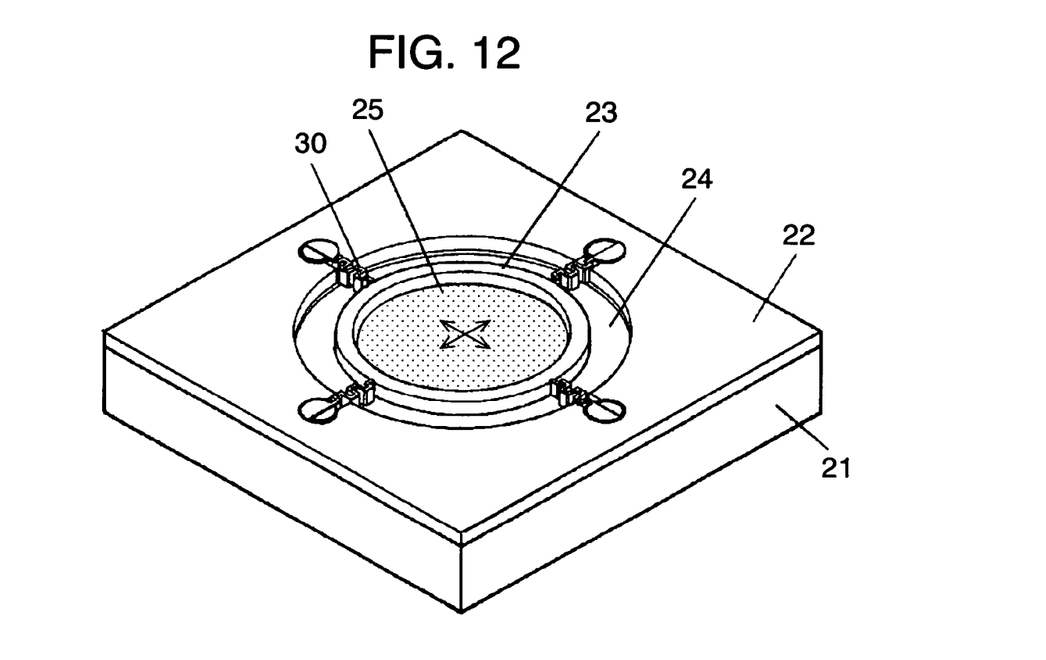
FIG. 12 shows a perspective view of a components separation device in accordance with an exemplary embodiment of the present invention.

As shown in FIG. 12, well 23 is not fixed to stage 21, but it is supported by supporting member 31 so that well 23 can move in glass cavity 24. Supporting member 31, at the one end, is connected fast on silicon base 22 at several points. Therefore, it can surely hold well 23. When it is provided at the crosswise directions, as shown in FIG. 12, well 23 can be moved in the crosswise directions.

Figure 13:
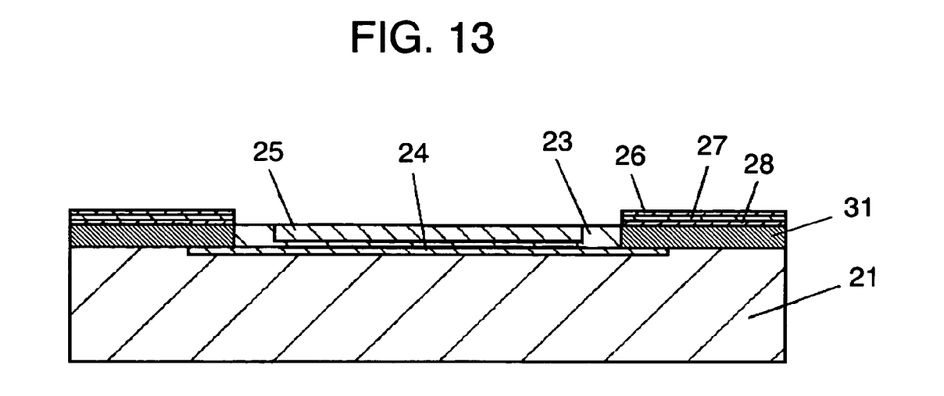
FIG. 13 shows a cross sectional view of a components separation device in accordance with an exemplary embodiment of the present invention.

As shown in FIG. 13, at least one pair of upper electrodes 26, piezoelectric layers 27, and lower electrodes 28 are provided on the upper surface of respective supporting member 31. Piezoelectric layer 27 is strained upon application of a certain voltage, and supporting member 31 is deformed as the result of bending stress. Actuator 30 is structured by taking advantage of the phenomena. Electrode pads 33, 34 are provided on silicon base 22 for applying voltage on actuator 30.

Supporting member 31 has been formed in a meander shape, as shown in FIG. 12, in order to provide the actuator with a largest possible amount of displacement possibility. However, it is not essential to take the meander shape.

(How to use 2)

A method to separate solid micro components is described using the above-configured separation device.

For separating liquid components or solid components contained in a mixture of different components using the above separation device, a vibration is given to well 23. The point of difference from embodiment 1 is in the direction of vibration of the well; the basic principle of separation remains the same. The particulars of separation are described referring to drawings. As shown in FIG. 13, actuator 30 has been provided on the upper surface of supporting member 31 using laminated piezoelectric element 40. When a certain voltage is applied between upper electrode 26 and lower electrode 28 via electrode pads 33 and 34, actuator 30 elongates/shrinks to move well 23 in the crosswise directions, as indicated with arrow marks in FIG. 12. Well 23 can be driven to make a vibration in the crosswise directions, by applying cyclical voltages on respective actuators 30 and synchronizing the motion of respective actuators 30.

When well 2 is vibrated, a sample of multiple components group stored in silicon cavity 25 is separated into respective components in accordance with different inertial forces generated in respective components. For example, when a sample consisting of a plurality of cells is put in silicon cavity 25 and vibrated, the sample is separated into cell components in accordance with difference in the inertial forces caused in respective components; the components are separated into a parallel arrangement according to the crosswise vibrating directions.

(How to manufacture 2)

A method for manufacturing a solid micro components separation device in accordance with embodiment 2 is described referring to FIG. 14 through FIG. 19.

As shown in FIG. 14, glass cavity 24 and glass base 32 are formed by etching glass stage 21. The etching may be conducted by dry-etching, wet-etching, etc.

Figure 15:
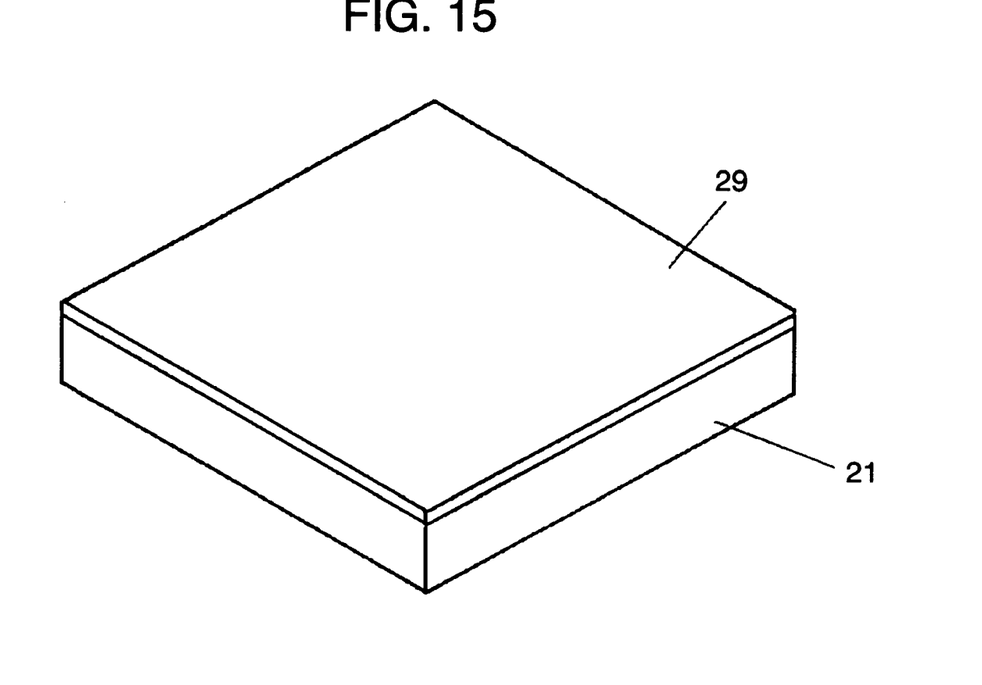
FIG. 15 is a perspective view of a components separation device, used to describe a method for manufacturing it in accordance with an exemplary embodiment of the present invention.

Next, as shown in FIG. 15, silicon substrate 29 is bonded on glass substrate. The bonding is made by the direct bonding method.

The surfaces of stage 21 and silicon substrate 29 are thoroughly cleaned before they are bonded together, using e.g. an acidic liquid of mixed sulfuric acid and hydrogen peroxide solution, or other alkaline liquid, so that there is no stain or dust remaining on the surfaces. Normally, the cleaning with the above-described acidic liquid is sufficient; however, there are some exceptional cases where the bonding is not possible depending on the surface roughness with the silicon and the glass. In such a case, the use of an alkaline liquid sometimes proves to be effective. An alkaline liquid etches silicon and glass, if slightly; so, a long time cleaning is not preferred. According to experimental results, it has been confirmed that a short time cleaning of approximately 10 min. results in a favorable bonding.

After the above cleaning is finished, the two substrates are put together and then heated at 200–500° C. Then, the interatomic bonding takes place between the silicon and the glass, and silicon substrate 29 is bonded fast to glass base 32.

Figure 16:
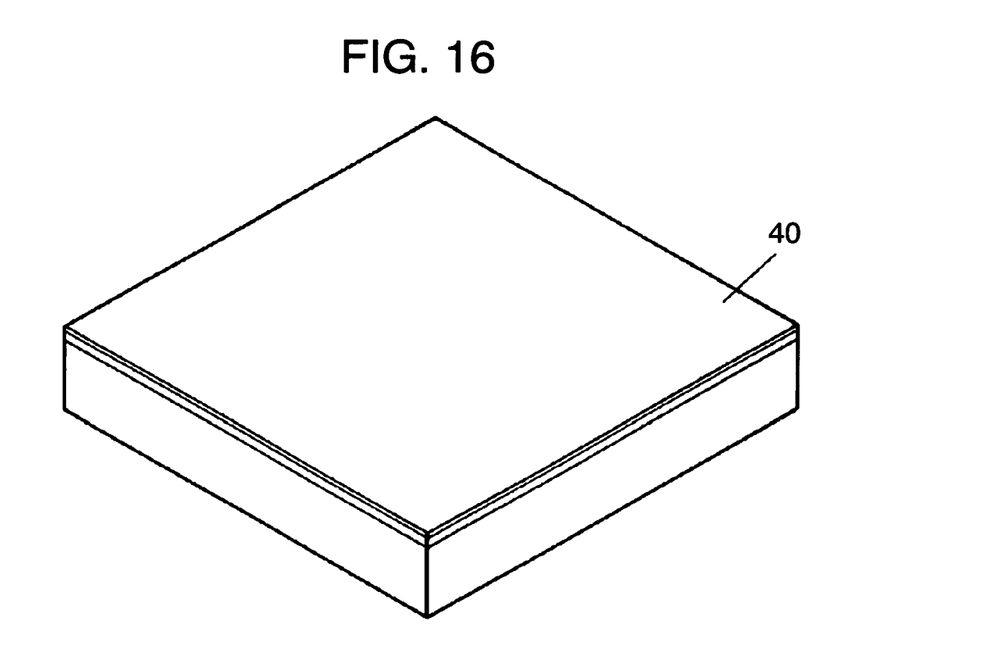
FIG. 16 is a perspective view of a components separation device, used to describe a method for manufacturing it in accordance with an exemplary embodiment of the present invention.

As shown in FIG. 16, laminated piezoelectric element 40 is formed by sputtering platinum for lower electrode 28, lead zirconate titanate for piezoelectric layer 27, and gold for upper electrode 26, in the order, on silicon substrate 29.

Figure 17:
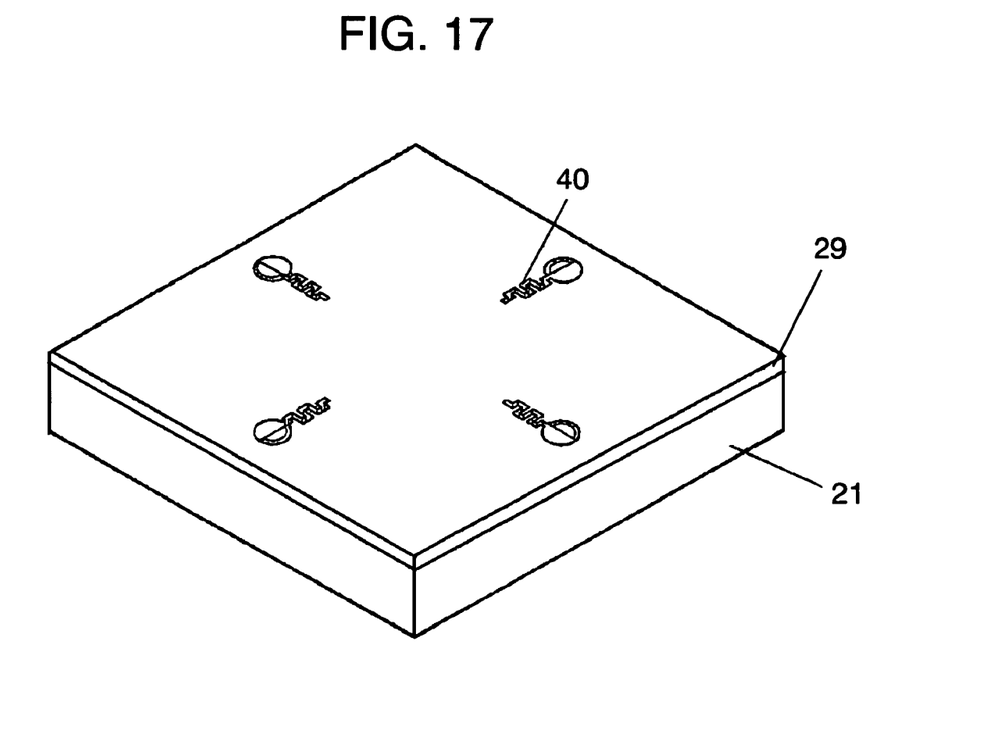
FIG. 17 is a perspective view of a components separation device, used to describe a method for manufacturing it in accordance with an exemplary embodiment of the present invention.

As shown in FIG. 17, laminated piezoelectric element 40 is processed into a meander shape, by etching upper electrode 26, piezoelectric layer 27, and lower electrode 28, one after the other. There are four units of meander shaped laminated piezoelectric bodies 40 shown in FIG. 17.

Figure 18:
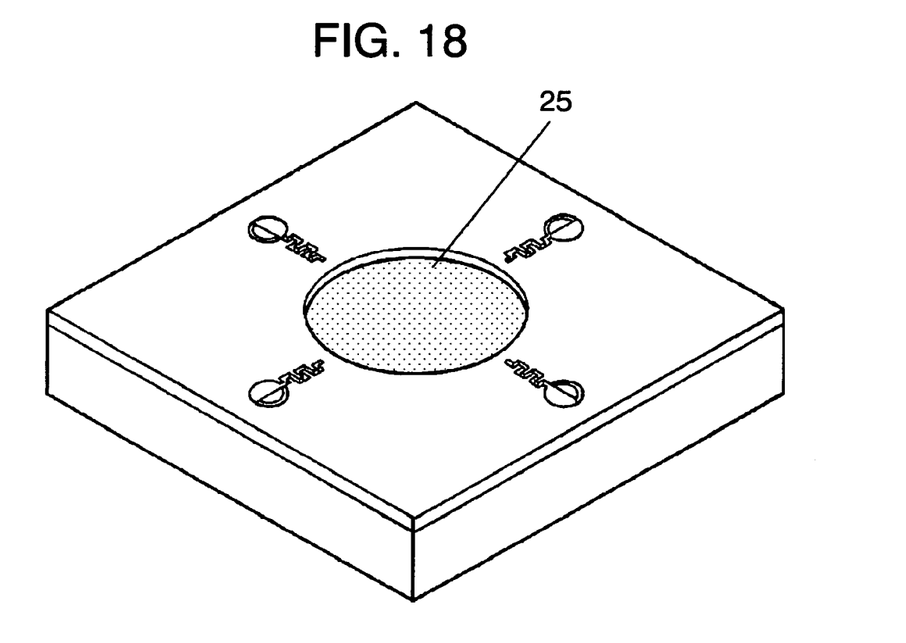
FIG. 18 is a perspective view of a components separation device, used to describe a method for manufacturing it in accordance with an exemplary embodiment of the present invention.

As shown in FIG. 18, silicon cavity 25 is formed by dry-etching silicon substrate 29 from the above. When, the depth of etching needs to be controlled to be a certain specific depth so that the bottom of silicon cavity 25 is not etched through silicon substrate 29. Thus, the bottom of silicon cavity 25 is formed with silicon substrate.

Figure 19:
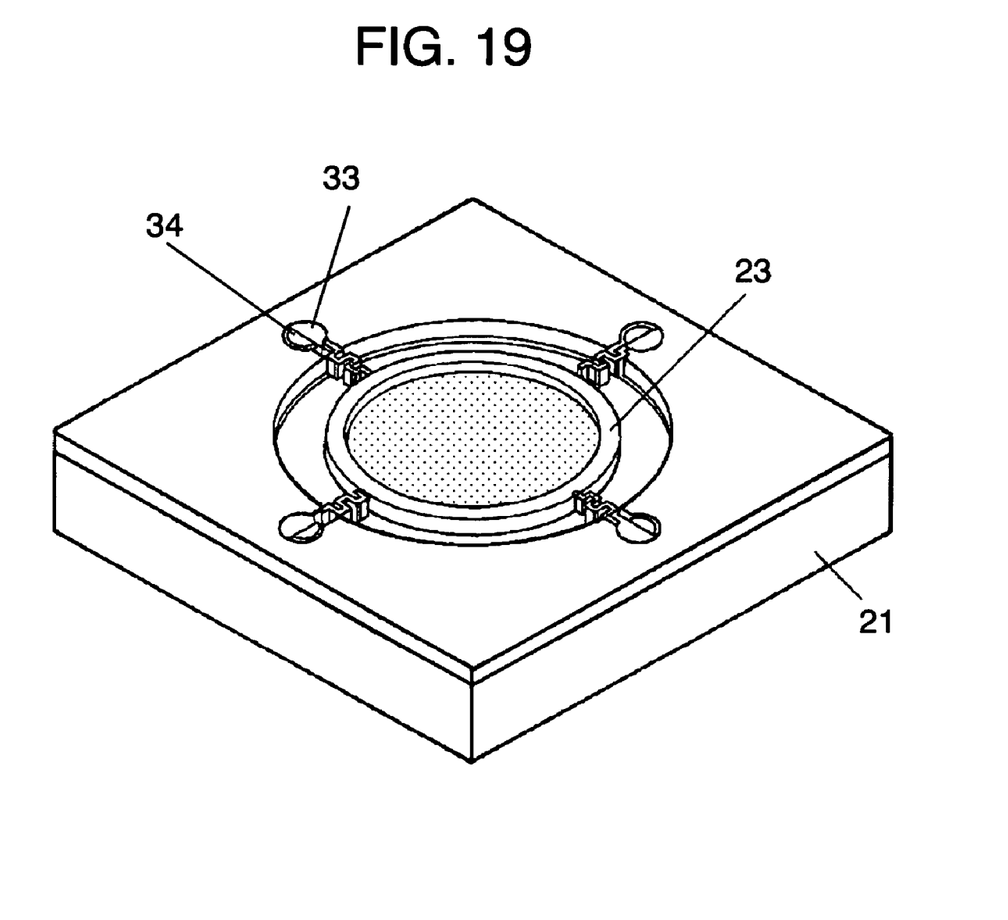
FIG. 19 is a perspective view of a components separation device, used to describe a method for manufacturing it in accordance with an exemplary embodiment of the present invention.

Next, as shown in FIG. 19, silicon substrate 29 is provided with a certain specific mask, and undergoes further dry-etching. Supporting member 31, well 23 and glass cavity 24 are provided by the present dry-etching process. For the portion of glass cavity 24, silicon substrate 29 is etched through to the bottom. Therefore, the bottom of glass cavity 24 is formed with glass substrate 21. Silicon substrate 29 corresponding to the bottom of meander-shaped laminated piezoelectric element 40 is processed likewise to the same shape. Actuator 30 is thus formed by silicon substrate 29 and laminated piezoelectric element 40, both processed to the same meander shape.

In this way, well 23 and silicon cavity 25 are provided, being supported by actuator 30 with a certain clearance against glass cavity 24.

In a solid micro components separation device thus finished, when laminated piezoelectric bodies 40 disposed on respective supporting members 31 are applied with certain voltage, each actuator 30, which has been formed by laminated piezoelectric element 40 and supporting member 31, elongates/shrinks to vibrate well 23 in the crosswise directions.

Thus it implements a solid micro components separation device which can separate cell components into parallel arrangements according to the crosswise vibrating directions.

INDUSTRIAL APPLICABILITY

As compared to the conventional centrifugal separators, a solid micro components separation device in the present invention can separate even a sample of very small amount into constituent components at a high accuracy level. In the conventional filter type separators, a certain specific filter having customized sizes and numbers in the holes has to be prepared for separating certain specific blood plasma/blood cells, for example. However, the present solid micro components separation device has a high versatility; it does not need to design e.g. a filter dedicated for separating a target component.

The invention claimed is:

1. A solid micro components separation device comprising
a stage,
a well having a certain specific volume on the stage,
a base fixed on the stage, and
an actuator connecting the base and the well; wherein
the well can contain at least two kinds of different components.

2. The components separation device of claim 1; wherein the well has a cavity of a certain specific volume, the cavity contains a mixture of a plurality of components, the mixture is separated into respective components when the well is vibrated by the actuator.

3. The components separation device of claim 1; wherein the well is driven by the actuator to move on a plane parallel to the stage in a rotating direction.

4. The components separation device of claim 3; wherein the actuator is formed by a fixed comb-teeth electrode connected to the base and an opposing electrode consisting of movable comb-teeth electrode connected to the well.

5. The components separation device of claim 3; wherein the movable comb-teeth electrode is led to the stage through a common electrode which is formed of one of the metals among gold, chromium, titanium and platinum.

6. The components separation device of claim 3; wherein the stage is further provided with a central axis connecting the well and the stage, and a plurality of the opposing electrodes.

7. The components separation device of claim 6; wherein one of the opposing electrodes and the other opposing electrode are applied respectively with different voltages cyclically so that the actuator vibrates the well in the rotating direction with the central axis as the center of revolution.

8. The components separation device of claim 1; wherein the well is driven by the actuator to move on a plane parallel to the stage in the crosswise directions.

9. The components separation device of claim 1; wherein the actuator comprises a piezoelectric element layer.

10. The components separation device of claim 9; wherein the actuator is formed in a laminated structure having a silicon substrate and the piezoelectric element layer, the piezoelectric element layer has a piezoelectric layer provided at the respective surfaces with an upper electrode and a lower electrode.

11. The components separation device of claim 10; wherein
the lower electrode is formed of platinum or titanium,
the piezoelectric layer is formed of lead zirconate titanate, and
the upper electrode is formed of gold, platinum, titanium or chromium.

12. The components separation device of claim 1; wherein the actuator has a meander shape.

13. The components separation device of claim 1; wherein the well is made of silicon material, the stage is made of glass material.

14. A method of separating solid micro components, using a components separation device comprising a stage, a well having a certain specific volume on the stage, a glass base fixed on the stage, and an actuator connecting the glass base and the well, the well having a silicon cavity of a certain specific volume; wherein
a sample consisting of solid components and liquid components contained in the well is vibrated by the actuator, and different components contained in the sample contained in the well are brought to uneven distribution and separated into respective components.

15. The method of separating solid micro components recited in claim 14, wherein the liquid component of sample is blood plasma, while the solid component is cells.

* * * * *